United States Patent [19]

Kaneko et al.

[11] 4,367,288
[45] Jan. 4, 1983

[54] METHOD FOR PRODUCING COENZYME $Q_{10}$

[75] Inventors: Yasuyuki Kaneko, Nagoya; Masao Ito, Anjyo, both of Japan

[73] Assignee: Nagoya University, Nagoya, Japan

[21] Appl. No.: 258,502

[22] Filed: Apr. 28, 1981

[30] Foreign Application Priority Data

May 16, 1980 [JP] Japan ................................. 55-65739

[51] Int. Cl.³ ........................ C12P 7/66; C12R 1/645
[52] U.S. Cl. ..................................... 435/133; 435/911
[58] Field of Search .......................................... 435/133

[56] References Cited

U.S. PATENT DOCUMENTS

| | | | |
|---|---|---|---|
| 3,769,170 | 10/1973 | Kondo et al. | 435/133 |
| 4,070,244 | 1/1978 | Nakao et al. | 435/133 |
| 4,205,125 | 5/1980 | Aida et al. | 435/133 |
| 4,220,719 | 9/1980 | Aida et al. | 435/133 |
| 4,245,048 | 1/1981 | Hata et al. | 435/133 |

FOREIGN PATENT DOCUMENTS

47-20396 6/1972 Japan .

*Primary Examiner*—Lionel M. Shapiro
*Attorney, Agent, or Firm*—Ladas & Parry

[57] ABSTRACT

Coenzyme $Q_{10}$ can be produced extremely quickly in exceedingly high yield in a simple industrial process by cultivating a microorganism of genus Aureobasidium or Trichosporon in a culture medium containing a large quantity of p-hydroxy benzoic acid.

18 Claims, 10 Drawing Figures

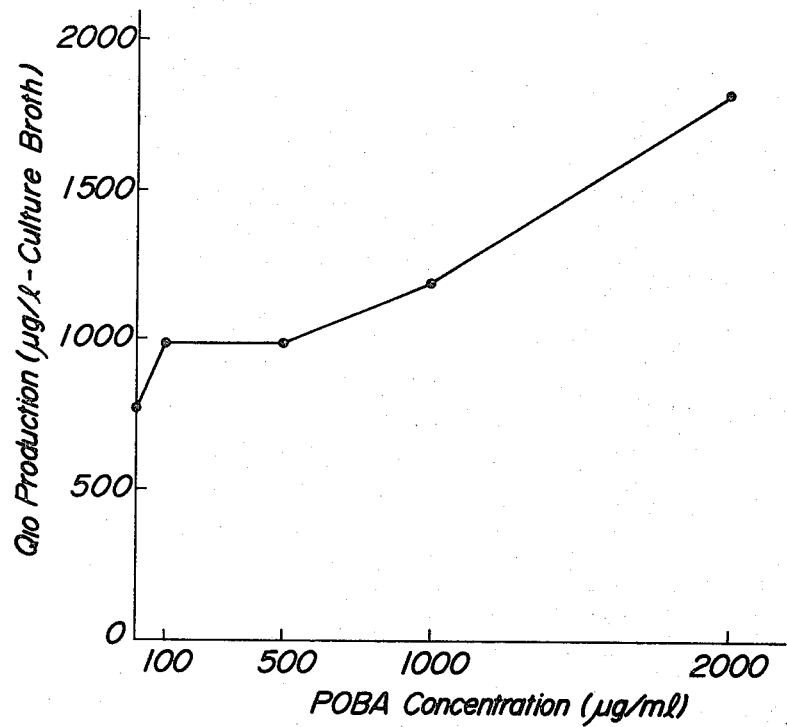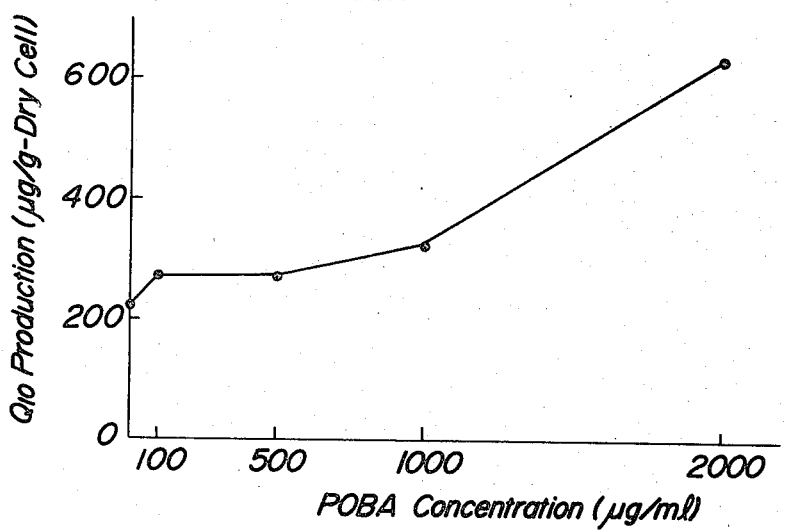

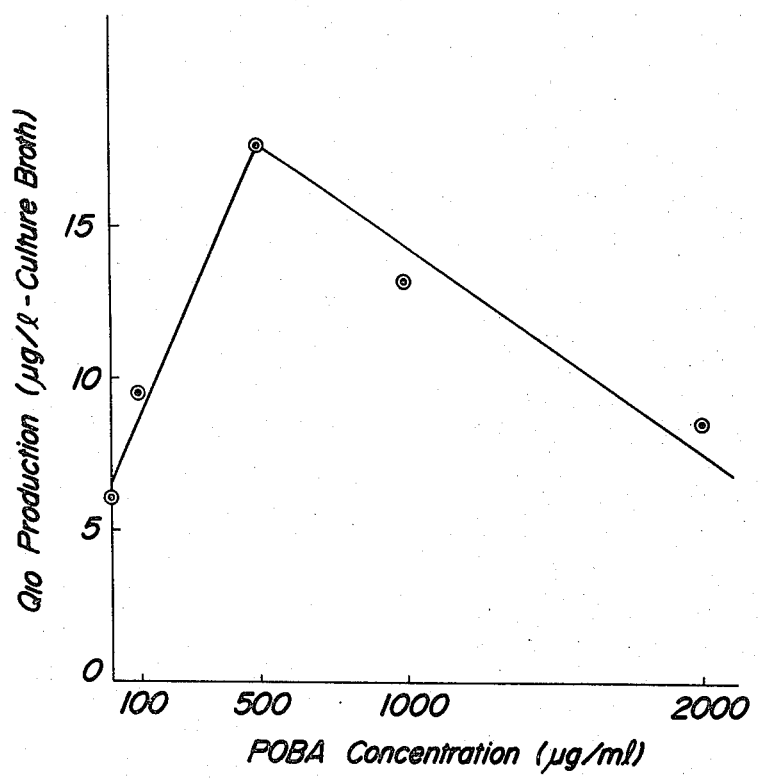
FIG_5A

METHOD FOR PRODUCING COENZYME $Q_{10}$

BACKGROUND OF THE INVENTION

The present invention relates to a method for producing coenzyme $Q_{10}$.

Recently, coenzyme $Q_{10}$ has been interested as a raw material for medicines for curing various diseases such as heart diseases, hypertension, tumor etc. and can be produced by various microorganisms. For example, Journal of Fermentation Technology, 47, p 553 (1969) discloses a method of improving productivity of coenzyme Q by adding as a component of culture medium p-hydroxybenzoic acid (abbreviated POBA) which is a precursor in a biosynthetic pathway of coenzyme $Q_{10}$. However, the method has a defect that the produced coenzyme Q is $Q_9$ and not $Q_{10}$. Coenzyme $Q_9$ is substantially inactive to human body and hence it does not exhibit the aforementioned desired pharmaceutical effects.

Japanese patent application publication No. 20,396/72 describes a method for producing coenzyme Q by cultivating a yeast, genus Candida capable of producing coenzyme Q in a culture medium containing n-alkane and POBA or POBA and acetic acid or its salt. However, production of coenzyme $Q_{10}$ is not disclosed and production of $Q_9$ or $Q_7$ as disclosed is limited due to the feature of using a yeast, genus Candida and to the fact that POBA has generally such a strong toxic property e.g. bactericidal property to microorganisms that it can be used as a food-preservative so that its addition is restricted to 5 mg/l at the most.

Japanese patent application publication No. 19,034/76 describes a method for producing coenzyme $Q_{10}$ by cultivating a microorganism of genus Alcaligenes, Trichosporon or Aureobasidium in a nutrient culture medium. However, the method has deficiencies of necessitating a pretreatment step of steam sterilizing the culture medium and thus necessitating a complicated production process.

SUMMARY OF THE INVENTION

An object of the present invention is to provide a method for producing coenzyme $Q_{10}$ in high yield in a culture medium containing a large quantity of POBA.

Another object of the present invention is to provide a method for producing coenzyme $Q_{10}$ quickly in a culture medium containing a large quantity of POBA.

Still another object of the present invention is to provide a method for producing coenzyme $Q_{10}$ in a simple industrial process in a culture medium containing a large quantity of POBA.

To achieve the above objects, the present invention provides a method for producing coenzmye $Q_{10}$ wherein coenzyme $Q_{10}$ is produced by cultivating a microorganism of genus Aureobasidium or Trichosporon in a culture medium containing a large quantity of POBA. According to the method of the present invention, the culture medium can also contain ethanol as a main carbon source in addition to POBA.

BRIEF DESCRIPTION OF THE DRAWINGS

FIGS. 1–5 are characteristic graphs showing relations between concentrations of POBA and production of coenzyme $Q_{10}$, corresponding respectively to data in Examples 1–5 which will be later described in detail.

DETAILED EXPLANATION OF THE INVENTION

Figure 2A:
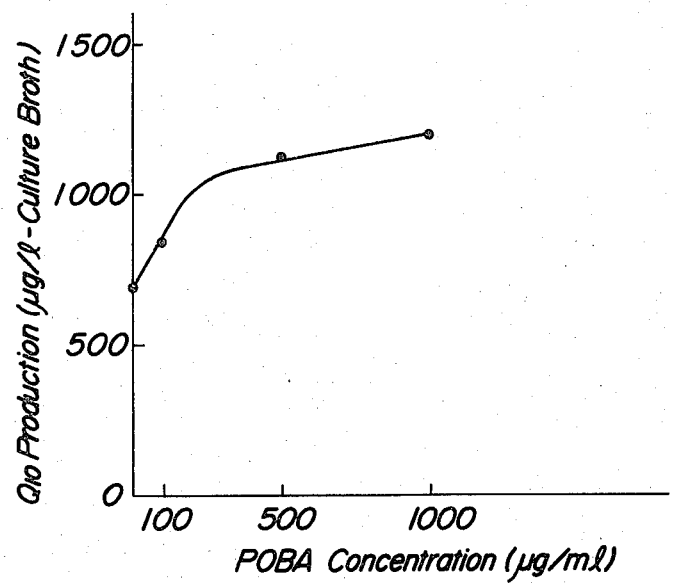

We have made various experiments and studies on relations between nutrient culture media and microorganisms for producing coenzyme $Q_{10}$, particularly of genera Aureobasidium and Trichosporon, leading to a finding that microorganisms of genera Aureobasidium and Trichosporon do not die even when POBA is added in such an amount that exceeds far beyond generally used. To the contrary, the productivity of coenzyme $Q_{10}$ is increased. It is quite surprising that microorganisms of genera Aureobasidium and Trichosporon can be tolerant to a high concentration of POBA, make growth and produce coenzyme $Q_{10}$ in exceedingly high yield.

Accordingly, in an aspect of the present invention, the present invention produces coenzyme $Q_{10}$ by cultivating a microorganism of genus Aureobasidium or Trichosporon in a culture medium wherein a large quantity of POBA is added to high concentration.

We have also found out that Aureobasidium sp. No. 14 strain which we deposited to Fermentation Research Institute (Fermentation Research Institute, Agency of Industrial Science and Technology, Ministry of International Trade and Industry) on Aug. 23, 1977 with deposit No. 4,197 is particularly suitable as a microorganism of genus Aureobasidium. With regard to this finding, we reported orally in the Annual Meeting of the Society of Japanese Agricultural Chemistry held in 1977 that the Aureobasidium sp. No. 14 strain exhibits strong tolerance to phenols and can utilize POBA as a sole carbon source, and filed a patent application as Japanese patent application No. 111,874/77. However, the oral report and the Japanese application disclosed merely assimilation or oxidization of phenols and growth of the Aureobasidium sp. No. 14 strain and did not disclose production of coenzyme $Q_{10}$.

We have found out also that Trichosporon sp. WY 2-2 strain which we deposited to Fermentation Research Institute on May 1, 1980 with deposit No. 5,500 is particularly suitable as a microorganism of genus Trichosporon.

We have found out also that POBA is preferably added in a concentration of about 1,000–4,000 $\mu g/ml$ to culture medium at a temperature of about 20°–37° C. when microorganism of genus Aureobasidium is used. If the concentration is less than about 1,000 $\mu g/ml$, the effect of addition can not be exhibited sufficiently to increase the production of coenzyme $Q_{10}$, while if the concentration is larger than about 4,000 $\mu g/ml$, the bactericidal property of POBA is exhibited so much and the growth is suppressed so that the growth rate decreases. A concentration of about 1,500–3,500 $\mu g/ml$ is particularly preferable. As for a microorganism of genus Trichosporon, we found out that POBA is preferably added in a concentration of about 250–1,000 $\mu g/ml$ to culture medium at a temperature of about 20°–37° C. If the concentration is less than about 250 $\mu g/ml$, the production of coenzyme $Q_{10}$ decreases, while if the concentration is larger than about 1,000 $\mu g/ml$, the bactericidal property of POBA is exhibited so much and the growth rate decreases. A concentration of about 400–800 $\mu g/ml$ is particularly preferable.

According to the present invention, any carbon source can be used as far as the microorganisms concerning the present invention can assimilate. For instance, use is made of carbohydrates such as starch etc.;

alcohols such as glycerol, propanol etc.; sugars such as glucose, sucrose, molasses etc.; hydrocarbons such as aliphatic and aromatic hydrocarbons; or organic acids such as palmitic acid, fumalic acid etc.

We have found out also that coenzyme $Q_{10}$ can be produced not only in extremely short period of time but also in exceedingly high yield, if ethanol is used as a carbon source in addition to POBA.

Accordingly, in another aspect of the present invention, the method of the present invention produces coenzyme $Q_{10}$ by cultivating a microorganism of genus Aureobasidium or Trichosporon in a culture medium containing ethanol as a main carbon source in addition to a large quantity of POBA.

It is quite surprising that, if ethanol is added to the culture medium, the growth rate increases remarkably to about twice as much of usual so that coenzyme $Q_{10}$ can be produced extremely quickly despite the bactericidal property of ethanol.

The concentration of ethanol to be added is about 0.5–4.0% (V/V) to the culture medium. If the concentration is less than about 0.5% (V/V), the amount of the cells produced becomes less. If the concentration is larger than about 4.0% (V/V), the bactericidal property of ethanol is exhibited so much and the growth is suppressed to decrease the growth rate. A concentration of about 1.0–3.0% (V/V) is particularly preferable.

In the present invention, the usual nitrogen source, vitamines, inorganic salts etc. generally used can be added in usual amounts to the culture medium.

Preferable cultivation conditions are a pH of about 2–8, a temperature of about 20°–37° C., the cultivation period of about 20–80 hrs. and an aerobic atmosphere.

If pH value varies noticeably during cultivation to suppress the growth of the cells, pH is preferably adjusted by addition of acidic or alkaline material.

DESCRIPTION OF THE PREFERRED EMBODIMENTS

Hereinafter, the present invention will be explained in more detail with reference to preferred embodiments which however should not be construed as limitations of the scope of the present invention.

In the succeeding examples, all quantities of materials are shown by gram unit, unless otherwise specified.

EXAMPLE 1

In this Example, Aureobasidium sp. No. 14 strain is used for producing coenzyme $Q_{10}$.

Inoculum cells are cultivated by the MPY medium which has the following composition.
 Composition of the MPY medium:
 Malt extract broth: 30
 Peptone: 5
 Yeast extract: 0.1
 Tap water: 1 l The culture medium used for pre-culture and main culture has the following composition.
 Composition of culture medium used for pre-culture and main culture:
 $NH_4NO_3$: 5.0
 $KH_2PO_4$: 2.5
 $MgSO_4.7H_2O$: 1.0
 NaCl: 0.1
 Yeast extract: 0.1
 $CaCl_2.2H_2O$: 0.01
 $FeCl_3.6H_2O$: 0.01
 $C_2H_5OH$: 20 ml POBA:
 0 (pre-culture)
 0–2,000 μg/ml (main culture)
Tap water: 980 ml
pH: 5.0

Cultivations are effected as follows.

A loopful cells from the young slant culture is inoculated to the MPY medium 10 ml, and cultivated at 30° C. for 7 days to obtain inoculum cells.

A drop of the inoculum cell suspension is inoculated to 200 ml of the above-mentioned pre-culture medium not containing POBA and subsequently subjected to shaking cultivation at 30° C. for 48 hrs. to yield a pre-culture broth.

The pre-culture broth is added to 800 ml of the aforementioned main culture medium containing POBA in a concentration of 0–2,000 μg/ml in a volume ratio of 1:4 to a total volume of 1 l and subjected again to shaking cultivation at 30° C. for 48 hrs.

The growth cells are separated from supernatant solution by centrifugal precipitation of the culture broth and washed three times with distilled water. Suspension of wet cells thus obtained are treated in the following procedure to give a raw sample for extracting coenzyme $Q_{10}$.

The mixture of 50 ml of the suspension of the wet cells, 150 ml of methanol, 5 g of pyrogallol and 20 g of sodium hydroxide are subjected to saponification by treating under a reflux condenser at 90° C. for 1 hr. and then extracted twice with each 100 ml of n-hexane. The n-hexane layer of total 200 ml is washed three times with distilled water, then dehydrated and dried overnight with anhydrous sodium sulfate, and thereafter concentrated under reduced pressure. The sample thus obtained is used for the quantitative analysis of coenzyme $Q_{10}$ in the following way.

The concentrate is dissolved in 7 ml of ethanol to give a sample solution.

2 ml of the sample solution, 0.5 ml of ethylcyanoacetate (ECA) and 0.5 ml of 0.2N-KOH aqueous solution are mixed. After exactly 10 min., Optional Density at 625 nm ($OD_{625}$) is determined. As a control, $OD_{625}$ is determined for a similar solution wherein instead of ECA an equal amount of ethanol is used and reacted in the same way. The control value is subtracted from the above determined value. The results are shown in Table 1.

TABLE 1

(Analytical results)

| POBA concentration (μg/ml) | Amount* of produced coenzyme $Q_{10}$ (μg) 1 l culture broth | Dry cell weight (g) 1 l culture broth | $Q_{10}$ production (μg) 1 g dry cell weight |
|---|---|---|---|
| 0 | 770 | 3.5 | 220 |
| 100 | 980 | 3.6 | 270 |
| 500 | 980 | 3.6 | 270 |
| 1,000 | 1,190 | 3.7 | 320 |
| 2,000 | 1,820 | 2.9 | 630 |

*Amount of coenzyme $Q_{10}$ obtained from 1 l culture broth.

The above results are also shown as characteristic graphs in the attached FIGS. 1A and 1B.

EXAMPLE 2

In this Example, the same microorganism and cultivation conditions as in Example 1 are used, and the same treatments as in Example 1 are effected, except that main culture is not adjusted to the pH value of 5.0 and conducted in an acidic condition of a pH value of 2.5–4.

A loopful cells from the young slant culture is inoculated to the MPY medium 10 ml, and cultivated at 30° C. for 7 days to obtain inoculum cells.

A drop of the inoculum cell suspension is inoculated to 200 ml of the pre-culture medium not containing POBA and subsequently subjected to shaking cultivation at 30° C. for 48 hrs. to yield a pre-culture broth.

The pre-culture broth is added to 800 ml of the main culture medium containing POBA in a concentration of 0–2,000 μg/ml and a pH value of 2.5–4.0 depending on POBA concentration in a volume ratio of 1:4 to a total volume of 1 l and subjected again to shaking cultivation at 30° C. for 48 hrs.

The cells are separated from supernatant solution by centrifugal precipitation of the culture broth and washed three times with distilled water. Suspension of wet cells thus obtained are treated in the following prcedure to give a raw sample for extracting coenzyme $Q_{10}$.

The mixture of 50 ml of the suspension of the wet cells, 150 ml of methanol, 5 g of pyrogallol and 20 g of sodium hydroxide are subjected to saponification by treating under a reflux condenser at 90° C. for 1 hr. and then extracted twice with each 100 ml of n-hexane. The n-hexane layer of total 200 ml is washed three times with distilled water, then dehydrated and dried overnight with anhydrous sodium sulfate, and thereafter concentrated under reduced pressure. The sample thus obtained is used for quantitative analysis of coenzyme $Q_{10}$ in the same way as in Example 1. The results are shown in Table 2.

TABLE 2

| POBA concentration (μg/ml) | (Analytical results) | | |
|---|---|---|---|
| | Amount* of produced coenzyme $Q_{10}$ (μg) 1 l culture broth | Dry cell weight (g) 1 l culture broth | $Q_{10}$ production (μg) 1 g dry cell weight |
| 0 | 700 | 2.5 | 280 |
| 100 | 840 | 2.6 | 320 |
| 500 | 1,120 | 2.1 | 530 |
| 1,000 | 1,190 | 2.1 | 570 |
| 2,000 | not grown | — | — |

*Amount of coenzyme $Q_{10}$ obtained from 1 l culture broth.

Figure 2B:
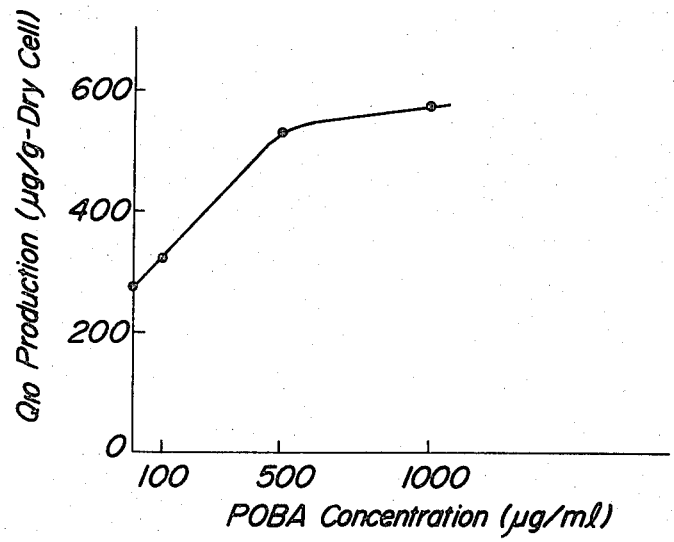

The above results are also shown as characteristic graphs in the attached FIGS. 2A and 2B.

EXAMPLE 3

The same experiment as in Example 1 is repeated, except that a loopful cells from the young slant culture is inoculated to 10 ml of the pre-culture medium not containing POBA instead of the MPY medium and cultivated at 30° C. for 10 days to obtain inoculum cells, and that POBA concentrations in the main culture medium is raised up.

A drop of the inoculum cell suspension is inoculated to 200 ml of the pre-culture medium not containing POBA and subsequently subjected to shaking cultivation at 30° C. for 48 hrs. to yield a pre-culture broth.

The pre-culture broth is added to 800 ml of the main culture medium containing POBA in a concentration of 1,000–4,000 μg/ml in a volume ratio of 1:4 to a total volume of 1 l and subjected again to shaking cultivation at 30° C. for 48 hrs.

The green cells are separated from supernatant solution by centrifugal precipitation of the culture broth and washed three times with distilled water. Suspension of wet cells thus obtained are treated in the following procedure to give a raw sample for extracting coenzyme $Q_{10}$.

The mixture of 50 ml of the suspension of the wet cells, 150 ml of methanol, 5 g of pyrogallol and 20 g of sodium hydroxide are subjected to saponification by treating under a reflux condenser at 90° C. for 1 hr. and then extracted twice with each 100 ml of n-hexane. The n-hexane layer of total 200 ml is washed three times with distilled water, then dehydrated and dried overnight with anhydrous sodium sulfate, and thereafter concentrated under reduced pressure. The sample thus obtained is used for quantitative analysis of coenzyme $Q_{10}$ in the same way as in Example 1.

The results are shown in Table 3.

TABLE 3

| POBA concentration (μg/ml) | (Analytical results) | | |
|---|---|---|---|
| | Amount* of produced coenzyme $Q_{10}$ (μg) 1 l culture broth | Dry cell weight (g) 1 l culture broth | $Q_{10}$ production (μg) 1 g dry cell weight |
| 1,000 | 2,310 | 7.1 | 330 |
| 2,000 | 3,920 | 5.5 | 710 |
| 3,300 | 3,220 | 5.8 | 560 |
| 4,000 | 2,940 | 7.3 | 400 |

*Amount of coenzyme $Q_{10}$ obtained from 1 l culture broth.

Figure 3A:
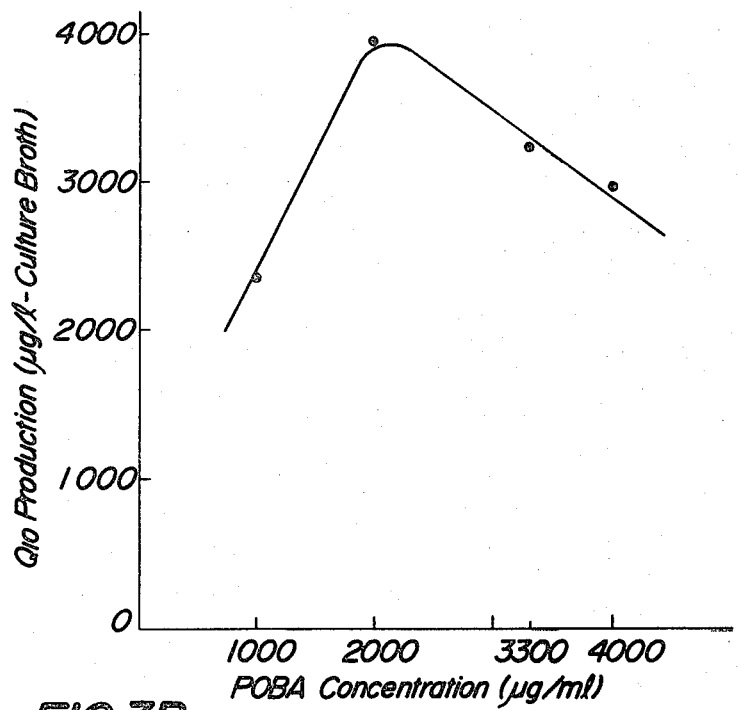
Figure 3B:
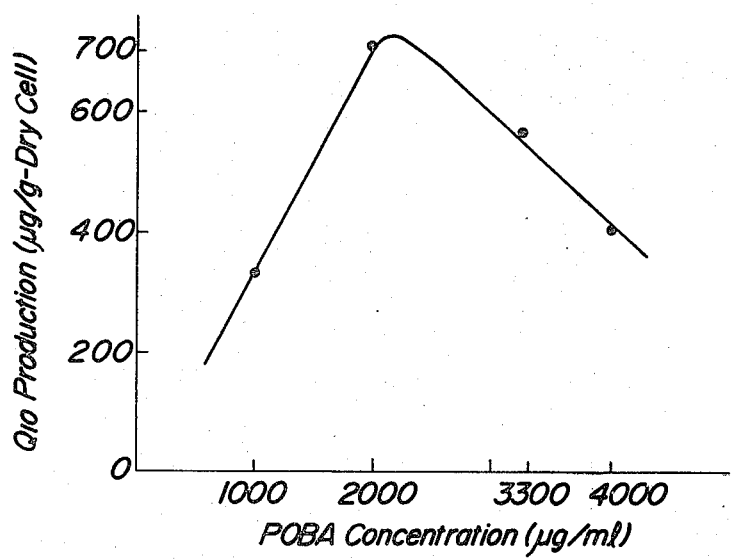

The above results are also shown as characteristic graphs in the attached FIGS. 3A and 3B.

EXAMPLE 4

The same experiment as in Example 3 is repeated, except that a loopful cells from the young slant culture is cultivated for 7 days instead of 10 days and that a temperature of 37° C. is used for the main cultivation instead of 30° C.

The results are shown in Table 4.

TABLE 4

| POBA concentration (μg/ml) | (Analytical results) | | |
|---|---|---|---|
| | Amount* of produced coenzyme $Q_{10}$ (μg) 1 l culture broth | Dry cell weight (g) 1 l culture broth | $Q_{10}$ production (μg) 1 g dry cell weight |
| 1,000 | 1,120 | 8.4 | 130 |
| 2,000 | 2,520 | 10.4 | 240 |
| 2,700 | 3,220 | 9.2 | 350 |
| 3,300 | 3,080 | 7.2 | 430 |
| 4,000 | 280 | 2.4 | 120 |

*Amount of coenzyme $Q_{10}$ obtained from 1 l culture broth.

Figure 4A:
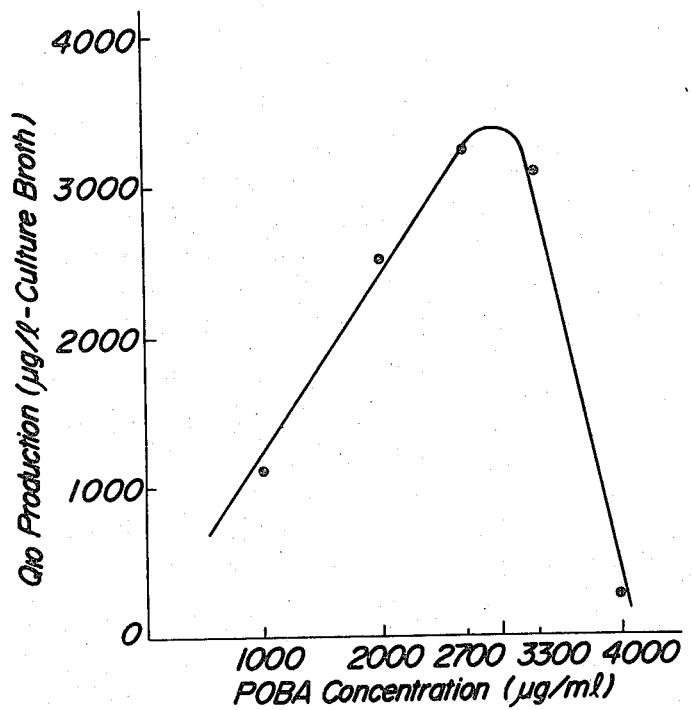
Figure 4B:
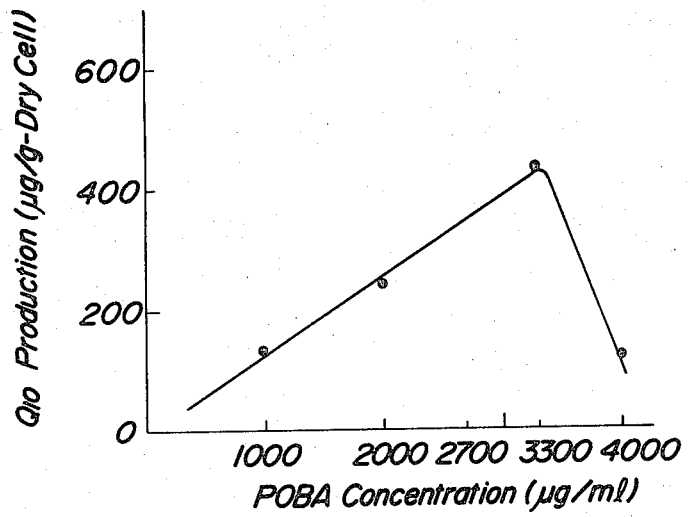

The above results are also shown as characteristic graphs in the attached FIGS. 4A and 4B.

EXAMPLE 5

In this Example, coenzyme $Q_{10}$ is produced using Trichosporon sp. WY 2-2 strain instead of Aureobasidium sp. No. 14 strain.

Cultivations are effected as follows.

A loopful cells from the young slant culture is inoculated to the aforementioned MPY medium 10 ml and cultivation at 30° C. for 7 days to obtain inoculum cells.

A drop of the inoculum cell suspension is inoculated to 200 ml of the above-mentioned pre-culture medium not containing POBA and subsequently subjected to shaking cultivation at 30° C. for 48 hrs. to yield a pre-culture broth.

The pre-culture broth is added to 800 ml of the aforementioned main culture medium containing POBA in a concentration of 0–2,000 µg/ml in a volume ratio of 1:4 to a total volume of 1 l and subjected again to shaking cultivation at 30° C. for 48 hrs.

The cells are separated from supernatant solution by centrifugal precipitation of the culture broth and washed three times with distilled water. Suspension of wet cells thus obtained is treated in the following procedure to give a raw sample for extracting coenzyme $Q_{10}$.

The mixture of 50 ml of the suspension of the wet cells, 150 ml of methanol, 5 g of pyrogallol and 20 g of sodium hydroxide are subjected to saponification by treating under a reflux condensor at 90° C. for 1 hr. and then extracted twice with each 100 ml of n-hexane. The n-hexane layer of total of 200 ml is washed three times with distilled water, then dehydrated and dried overnight with anhydrous sodium sulfate, and thereafter concentrated under reduced pressure. The sample thus obtained is used for quantitative analysis of coenzyme $Q_{10}$ in the following way.

The concentration is dissolved in 2 ml of acetone to give a sample solution. Ten µl of the sample solution is used for the quantitative analysis by high performance liquid chromatography. The quantitative value is determined by the standard curve obtained from the authentic specimen.

The results are shown in Table 5.

TABLE 5

(Analytical results)

| POBA concentration (µg/ml) | Amount* of produced coenzyme $Q_{10}$ (µg) 1 l culture broth | Dry cell weight (g) 1 l culture broth | $Q_{10}$ production (µg) 1 g dry cell weight |
|---|---|---|---|
| 0 | 6.03 | 0.053 | 114.0 |
| 100 | 9.50 | 0.098 | 97.0 |
| 500 | 17.80 | 0.173 | 103.0 |
| 1,000 | 13.20 | 0.190 | 69.4 |
| 2,000 | 8.52 | 0.181 | 47.0 |

*Amount of coenzyme $Q_{10}$ obtained from 1 l culture broth.

Figure 5B:
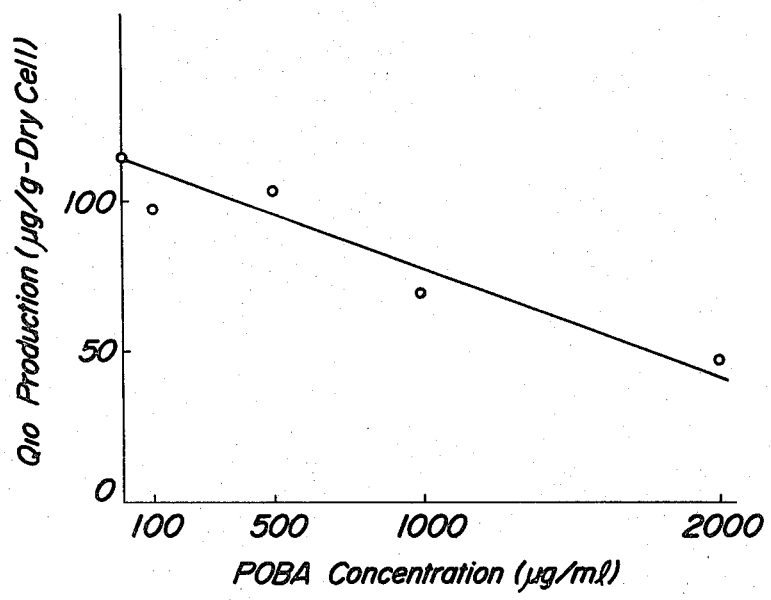

The above results are also shown as characteristic graphs in the attached FIGS. 5A and 5B.

REFERENTIAL EXAMPLE

Growth characteristics of Aureobasidium sp. No. 14 strain is studied on various utilizable main carbon sources other than ethanol. The main carbon sources used are glycerol, glucose, n-paraffin mixture (Carbon number $C_{11} \sim C_{14}$), n-propanol, acetone, ethyl acetate, cyclohexanol, n-dodecane or palmitic acid.

Cultivations are effected as follows.

A drop of the inoculum cell suspension obtained in the same procedure as in Example 1 is inoculated to 10 ml of a culture medium which has the same composition employed in Example 1 for pre-culture, except that as a main carbon source 20 ml of ethanol is replaced by 20 g or 20 ml of the above mentioned materials.

When the main carbon source used is insoluble in water, 0.5 g surfactant, Tween 80 is added per 1 l medium.

The inoculated culture medium is subjected to shaking cultivation at 30° C. and cell growth expressed in $OD_{660}$ unit and the cultivation time are observed.

The results are shown in Table 6.

TABLE 6

(Growth characteristics on various main carbon sources)

| Main carbon source | Growth ($OD_{660}$) | Cultivation time (hrs.) |
|---|---|---|
| glycerol | 4.14 | 54 |
| glucose | 4.46 | 54 |
| n-paraffin ($C_{11} \sim C_{14}$) | 2.86 | 54 |
| n-propanol | 2.50 | 248 |
| acetone | 1.02 | 248 |
| ethylacetate | 2.29 | 96 |
| cyclohexanol | 0.17 | 224 |
| n-dodecane | 3.54 | 54 |
| palmitic acid | 3.64 | 73 |

EXAMPLE 6

In this Example, coenzyme $Q_{10}$ is produced by Aureobasidium sp. No. 14 strain grown in the media containing various main carbon sources and a large quantity of POBA, 2,000 µg/ml. The main carbon sources used are glycerol, glucose or n-paraffin ($C_{11} \sim C_{14}$).

Cultivation is effected in the same way as in Referential Example to obtain 100 ml of a pre-culture broth.

The pre-culture broth thus obtained is added to 400 ml of the culture medium described in Referential Example containing POBA in the concentration of 2,000 µg/ml in a volume ratio of 1:4 to a total volume of 500 ml and subjected again to shaking cultivation at 30° C. for a given period.

The grown cells are separated from supernatant solution by centrifugal precipitation of the culture broth and washed three times with distilled water. Suspension of wet cells thus obtained are treated in the same procedure as in Example 1 to give a raw sample for extracting and quantitative analysis of coenzyme $Q_{10}$.

The results are shown in Table 7.

TABLE 7

(Production of $Q_{10}$ on various main carbon sources)

| Main carbon source | Pre-culture (hrs.) | Main culture (hrs.) | Wet cell weight (g) | $Q_{10}$ (µg/l) |
|---|---|---|---|---|
| glycerol | 42 | 52 | 14.2 | 2,900 |
| glucose | 47 | 47 | 10.0 | 1,900 |
| n-paraffin ($C_{11} \sim C_{14}$) | 47 | 70 | 1.4 | 100 |

As clearly indicated from the above quantitative analytical results, the present invention is exceedingly superior to conventional methods.

Although the present invention has been explained in detail with specific values and embodiments, it will of course be apparent to those skilled in the art that many variations and modifications are possible without departing from the broad aspect and scope of the present invention as defines in the appended claims.

What is claimed is:

1. A method for producing coenzyme $Q_{10}$ comprising cultivating a microorganism selected from the group consisting of Aureobasidium sp. No. 14 strain and Trichosporon sp. WY 2-2 strain in a culture medium containing a large quantity of about 250 to 4,000 μg/ml of p-hydroxybenzoic acid to produce coenzyme $Q_{10}$.

2. A method as defined in claim 1, wherein the microorganism of Aureobasidium sp. No. 14 strain is cultivated in the culture medium containing p-hydroxybenzoic acid in a concentration of about 1,000–4,000 μg/ml at a temperature of about 20°–37° C.

3. A method as defined in claim 1, wherein the microorganism of Trichosporon sp. WY 202 strain is cultivated in the culture medium containing p-hydroxybenzoic acid in a concentration of about 250–1,000 μg/ml at a temperature of about 20°–37° C.

4. A method for producing coenzyme $Q_{10}$, comprising cultivating a microorganism selected from the group consisting of Aureobasidium sp. No. 14 strain and Trichosporon sp. WY 2-2 strain in a culture medium containing a large quantity of about 250 to 4,000 μg/ml of p-hydroxybenzoic acid to which ethanol is added as a main carbon source to produce coenzyme $Q_{10}$.

5. A method as defined in claim 4, wherein the microorganism of Aureobasidium sp. No. 14 strain is cultivated in the culture medium containing p-hydroxybenzoic acid in a concentration of about 1,000–4,000 μg/ml at a temperature of about 20°–37° C.

6. A method as defined in claim 4, wherein the microorganism of Trichosporon sp. WY 2-2 strain is cultivated in the culture medium containing p-hydroxybenzoic acid in a concentration of about 250–1,000 μg/ml at a temperature of about 20°–37° C.

7. A method as defined in claim 1, wherein a concentration of p-hydroxybenzoic acid is about 1,500–3,500 μg/ml.

8. A method as defined in claim 3, wherein a concentration of p-hydroxybenzoic acid is about 400–800 μg/ml.

9. A method as defined in claim 1, wherein the cultivation is effected at a pH value of about 2–8.

10. A method as defined in claim 1, wherein the cultivation is effected in an aerobic atmosphere for about 20–80 hrs.

11. A method as defined in claim 1, wherein the culture medium is added with a material selected from the group consisting of acidic material and alkaline material during the cultivation.

12. A method as defined in claim 5, wherein the concentration of p-hydroxybenzoic acid is about 1,500–3,500 μg/ml.

13. A method as defined in claim 6, wherein the concentration of p-hydroxybenzoic acid is about 400–800 μg/ml.

14. A method as defined in claim 4, wherein ethanol is added to the culture medium in a concentration of about 0.5–4.0% by volume.

15. A method as defined in claim 14, wherein ethanol is added to the culture medium in a concentration of about 1.0–3.0% by volume.

16. A method as defined in claim 4, wherein the cultivation is effected at a pH value of about 2–8.

17. A method as defined in claim 4, wherein the cultivation is effected in an aerobic atmosphere for about 20–80 hrs.

18. A method as defined in claim 4, wherein the culture medium is added with a material selected from the group consisting of acidic material and alkaline material during the cultivation.

* * * * *